United States Patent
Wilbur et al.

(10) Patent No.: US 11,826,582 B2
(45) Date of Patent: *Nov. 28, 2023

(54) REVOLVING RADIATION COLLIMATOR

(71) Applicant: Zap Surgical Systems, Inc., San Carlos, CA (US)

(72) Inventors: Raymond Wilbur, San Jose, CA (US); Younes Achkire, San Francisco, CA (US); Manoocher Birang, San Carlos, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/313,453

(22) Filed: May 6, 2021

(65) Prior Publication Data

US 2021/0322790 A1    Oct. 21, 2021

Related U.S. Application Data

(63) Continuation of application No. 15/971,861, filed on May 4, 2018, now Pat. No. 11,058,892.

(Continued)

(51) Int. Cl.
*A61N 5/10* (2006.01)
*G01B 11/27* (2006.01)
(Continued)

(52) U.S. Cl.
CPC ......... *A61N 5/1042* (2013.01); *A61N 5/1081* (2013.01); *G01B 11/27* (2013.01);
(Continued)

(58) Field of Classification Search
CPC ...... A61N 5/10–1084; A61N 2005/1085–1098
See application file for complete search history.

(56) References Cited

U.S. PATENT DOCUMENTS

| 2,595,260 A | 5/1952 | Hollstein |
| 2,781,454 A | 2/1957 | Green et al. |
| 2,818,510 A | 12/1957 | Hansheinrich |
| 2,890,349 A | 6/1959 | Laszlo |
| 3,082,322 A | 3/1963 | Koerner et al. |

(Continued)

FOREIGN PATENT DOCUMENTS

| CN | 2533895 Y | 2/2003 |
| CN | 1481756 A | 3/2004 |

(Continued)

OTHER PUBLICATIONS

Bodduluri et al., "X-ray guided robotic radiosurgery for solid tumors", Industrial Robot: An International Journal, vol. 29, No. 3, 2002, pp. 221-227.

(Continued)

*Primary Examiner* — Thaddeus B Cox
(74) *Attorney, Agent, or Firm* — Kilpatrick Townsend & Stockton LLP

(57) ABSTRACT

Devices, systems and method that allow for delivery of therapeutic radiation beams of differing sizes or shapes during a radiation treatment are provided herein. Such devices can include a rotatable collimator body having multiple collimator channels of differing size or shape defined therein, the channels extending through the collimator body substantially perpendicular to the axis of rotation. The collimator body can include markers thereon to facilitate detection of an alignment position by a sensor of a control system to allow the collimator body to be rapidly and accurately moved between alignment positions to facilitate delivery of differing therapy beams during a treatment.

30 Claims, 5 Drawing Sheets

Related U.S. Application Data

(60) Provisional application No. 62/502,472, filed on May 5, 2017.

(51) Int. Cl.
  *G21K 1/02* (2006.01)
  *G21K 1/04* (2006.01)

(52) U.S. Cl.
  CPC .............. *G21K 1/025* (2013.01); *G21K 1/046* (2013.01); *A61N 2005/1095* (2013.01)

(56) References Cited

U.S. PATENT DOCUMENTS

| | | | |
|---|---|---|---|
| 3,281,598 A | 10/1966 | Irene | |
| 3,349,242 A | 10/1967 | Braestrup | |
| 3,466,439 A | 9/1969 | Setala | |
| 3,488,495 A | 1/1970 | Schneeman | |
| 3,588,499 A | 6/1971 | Pegrum | |
| 3,617,749 A | 11/1971 | Massiot | |
| 3,670,163 A | 6/1972 | Lajus | |
| 3,803,418 A | 4/1974 | Holstrom | |
| 3,833,813 A | 9/1974 | James | |
| 3,852,598 A | 12/1974 | Larsson | |
| 3,868,506 A | 2/1975 | Ogiso | |
| 3,892,967 A | 7/1975 | Howarth et al. | |
| 4,139,775 A | 2/1979 | Williams | |
| 4,177,382 A | 12/1979 | Hounsfield | |
| 4,209,706 A | 6/1980 | Nunan | |
| 4,266,135 A | 5/1981 | Kuwik et al. | |
| 4,288,700 A | 9/1981 | Grass et al. | |
| 4,338,521 A | 7/1982 | Shaw et al. | |
| 4,339,825 A | 7/1982 | Barrett et al. | |
| 4,358,856 A | 11/1982 | Stivender et al. | |
| 4,363,128 A | 12/1982 | Grady et al. | |
| 4,481,656 A | 11/1984 | Janssen et al. | |
| 4,541,108 A | 9/1985 | Grady et al. | |
| 4,560,882 A | 12/1985 | Barbaric et al. | |
| 4,649,560 A | 3/1987 | Grady et al. | |
| 4,653,083 A | 3/1987 | Rossi | |
| 4,741,015 A | 4/1988 | Charrier | |
| 4,741,105 A | 5/1988 | Wong | |
| 4,756,016 A | 7/1988 | Grady et al. | |
| 4,827,491 A | 5/1989 | Barish | |
| 4,866,751 A | 9/1989 | Louiday | |
| 4,922,512 A | 5/1990 | Lajus et al. | |
| 4,977,585 A | 12/1990 | Boyd | |
| 4,987,585 A | 1/1991 | Kidd et al. | |
| 4,998,268 A | 3/1991 | Winter | |
| 5,038,371 A | 8/1991 | Janssen et al. | |
| 5,040,203 A | 8/1991 | Janssen et al. | |
| 5,048,069 A | 9/1991 | Siczek | |
| 5,048,071 A | 9/1991 | Van | |
| 5,052,036 A | 9/1991 | Grady | |
| 5,054,041 A | 10/1991 | Hampel | |
| 5,073,917 A | 12/1991 | Van et al. | |
| 5,086,447 A | 2/1992 | Siczek et al. | |
| 5,095,501 A | 3/1992 | Kobayashi | |
| 5,155,757 A | 10/1992 | Sakaniwa et al. | |
| 5,159,622 A | 10/1992 | Sakaniwa et al. | |
| 5,207,223 A | 5/1993 | Adler et al. | |
| 5,379,333 A | 1/1995 | Toth | |
| 5,420,427 A | 5/1995 | Morgan et al. | |
| 5,537,452 A | 7/1996 | Shepherd et al. | |
| 5,577,094 A | 11/1996 | Fudamoto | |
| 5,634,929 A | 6/1997 | Misko et al. | |
| 5,699,446 A | 12/1997 | Rougee et al. | |
| 5,751,781 A | 5/1998 | Brown et al. | |
| 5,757,886 A * | 5/1998 | Song .................. | A61N 5/1084 378/150 |
| 5,835,557 A | 11/1998 | Malmstroem | |
| 5,945,684 A | 8/1999 | Lam et al. | |
| 6,104,779 A | 8/2000 | Shepherd et al. | |
| 6,155,713 A | 12/2000 | Watanabe | |
| 6,198,957 B1 | 3/2001 | Green | |
| 6,217,214 B1 | 4/2001 | Cabral et al. | |
| 6,309,102 B1 | 10/2001 | Stenfors | |
| 6,325,538 B1 | 12/2001 | Heesch | |
| 6,512,813 B1 * | 1/2003 | Krispel .................... | G21K 1/04 378/65 |
| 6,614,871 B1 | 9/2003 | Kobiki et al. | |
| 6,789,941 B1 | 9/2004 | Grady | |
| 6,856,670 B2 | 2/2005 | Hoheisel | |
| 6,888,919 B2 | 5/2005 | Graf | |
| 6,969,194 B1 | 11/2005 | Naefstadius | |
| 7,188,999 B2 | 3/2007 | Mihara et al. | |
| 7,193,227 B2 | 3/2007 | Hiramoto et al. | |
| 7,239,684 B2 | 7/2007 | Hara et al. | |
| 7,295,648 B2 | 11/2007 | Brown | |
| 7,302,038 B2 | 11/2007 | Mackie et al. | |
| 7,473,913 B2 | 1/2009 | Hermann et al. | |
| 7,502,443 B1 | 3/2009 | Haynes et al. | |
| 7,526,066 B2 | 4/2009 | Koshnitsky et al. | |
| 7,649,981 B2 | 1/2010 | Seppi et al. | |
| 8,139,714 B1 | 3/2012 | Sahadevan | |
| 8,406,844 B2 | 3/2013 | Ruchala et al. | |
| 8,602,647 B2 | 12/2013 | Navarro | |
| 8,913,716 B2 | 12/2014 | Sobering et al. | |
| 9,014,341 B2 | 4/2015 | Zhang et al. | |
| 9,208,918 B2 | 12/2015 | Tybinkowski et al. | |
| 9,308,395 B2 | 4/2016 | Adler, Jr. et al. | |
| 9,314,160 B2 | 4/2016 | Adler, Jr. et al. | |
| 9,604,077 B2 | 3/2017 | Xing et al. | |
| 9,757,593 B2 | 9/2017 | Adler et al. | |
| 10,499,861 B2 | 12/2019 | Achkire et al. | |
| 2004/0066889 A1 | 4/2004 | Swift | |
| 2004/0136495 A1 * | 7/2004 | Carlsson .................. | G21K 1/04 378/65 |
| 2004/0149924 A1 | 8/2004 | Russell | |
| 2004/0170254 A1 | 9/2004 | Gregerson et al. | |
| 2004/0251419 A1 | 12/2004 | Nelson et al. | |
| 2005/0049477 A1 | 3/2005 | Fu et al. | |
| 2005/0141671 A1 * | 6/2005 | Pastyr .................... | G21K 1/046 378/148 |
| 2005/0197564 A1 | 9/2005 | Dempsey | |
| 2005/0236588 A1 | 10/2005 | Ein-Gal | |
| 2006/0245548 A1 | 11/2006 | Callerame et al. | |
| 2007/0014391 A1 | 1/2007 | Mostafavi et al. | |
| 2007/0189591 A1 | 8/2007 | Lu et al. | |
| 2008/0002809 A1 | 1/2008 | Bodduluri | |
| 2008/0144908 A1 | 6/2008 | West et al. | |
| 2008/0212738 A1 | 9/2008 | Gertner et al. | |
| 2009/0086909 A1 | 4/2009 | Hui et al. | |
| 2009/0103686 A1 | 4/2009 | Rothschild | |
| 2009/0110146 A1 | 4/2009 | Sliski et al. | |
| 2009/0163799 A1 | 6/2009 | Erbel et al. | |
| 2009/0180678 A1 | 7/2009 | Kuduvalli et al. | |
| 2010/0002829 A1 | 1/2010 | Dafni | |
| 2010/0094119 A1 | 4/2010 | Yu et al. | |
| 2010/0183196 A1 | 7/2010 | Fu et al. | |
| 2010/0237259 A1 | 9/2010 | Wang | |
| 2010/0239066 A1 | 9/2010 | Conolly et al. | |
| 2010/0268074 A1 | 10/2010 | Van Loef et al. | |
| 2011/0210261 A1 | 9/2011 | Maurer | |
| 2013/0114872 A1 | 5/2013 | Chen et al. | |
| 2013/0136239 A1 | 5/2013 | Laws et al. | |
| 2013/0188856 A1 | 7/2013 | Adler, Jr. et al. | |
| 2013/0261430 A1 | 10/2013 | Uhlemann | |
| 2014/0140471 A1 | 5/2014 | Tybinkowski et al. | |
| 2015/0265852 A1 * | 9/2015 | Meir ..................... | A61B 90/39 348/46 |
| 2016/0095558 A1 | 4/2016 | Choy et al. | |
| 2016/0220848 A1 | 8/2016 | Adler, Jr. et al. | |
| 2016/0317839 A1 | 11/2016 | Prionas et al. | |
| 2017/0281972 A1 | 10/2017 | Zhang et al. | |
| 2018/0318607 A1 | 11/2018 | Wilbur et al. | |
| 2019/0001146 A1 | 1/2019 | Liu | |
| 2020/0038685 A1 | 2/2020 | Kundapur et al. | |

FOREIGN PATENT DOCUMENTS

| | | |
|---|---|---|
| CN | 1666301 A | 9/2005 |
| CN | 2772541 Y | 4/2006 |

(56) References Cited

FOREIGN PATENT DOCUMENTS

| | | | |
|---|---|---|---|
| CN | 1785454 A | 6/2006 | |
| CN | 1810320 A | 8/2006 | |
| CN | 1919372 A | 2/2007 | |
| CN | 101069644 | 11/2007 | |
| CN | 101496727 A | 8/2009 | |
| CN | 102441238 A | 5/2012 | |
| CN | 103185914 | 7/2013 | |
| CN | 106237545 | 12/2016 | |
| CN | 106267587 | 1/2017 | |
| CN | 106456991 A | 2/2017 | |
| CN | 106512221 A | 3/2017 | |
| CN | 106908827 | 6/2017 | |
| CN | 107101712 | 8/2017 | |
| CN | 108401421 | 8/2018 | |
| DE | 3321057 A1 | 12/1984 | |
| DE | 19604789 A1 * | 8/1997 | ........... A61N 5/1084 |
| DE | 19728788 A1 | 1/1999 | |
| EP | 1075855 A1 | 2/2001 | |
| FR | 1587608 A | 3/1970 | |
| GB | 1129653 A | 10/1968 | |
| JP | 6082300 U | 6/1985 | |
| JP | 01502401 | 8/1989 | |
| JP | 04221532 A | 8/1992 | |
| JP | 2885304 B2 | 12/1993 | |
| JP | 0767975 A | 3/1995 | |
| JP | 07163669 A | 6/1995 | |
| JP | H07255867 A | 10/1995 | |
| JP | H07265445 A | 10/1995 | |
| JP | 2000271109 A | 10/2000 | |
| JP | 2001137372 A | 5/2001 | |
| JP | 2003024459 A | 1/2003 | |
| JP | 2003205042 A | 7/2003 | |
| JP | 2003210596 | 7/2003 | |
| JP | 2004097646 A | 4/2004 | |
| JP | 2007148276 A | 6/2007 | |
| JP | 2010519965 | 6/2010 | |
| JP | 2012183283 | 9/2012 | |
| NL | 7215879 | 5/1973 | |
| WO | 0074779 A1 | 12/2000 | |
| WO | 0112262 A1 | 2/2001 | |
| WO | 03018131 A1 | 3/2003 | |
| WO | 2003077763 | 9/2003 | |
| WO | 2008024463 | 2/2008 | |
| WO | 2012040964 A1 | 4/2012 | |
| WO | WO-2012040964 A1 * | 4/2012 | ........... A61N 5/1042 |
| WO | 2013180883 A1 | 12/2013 | |
| WO | 2015096572 A1 | 7/2015 | |
| WO | 2017020244 A1 | 2/2017 | |
| WO | 2017041750 A1 | 3/2017 | |
| WO | 2017083026 | 5/2017 | |
| WO | 2017100611 A1 | 6/2017 | |
| WO | 2018/203918 A1 | 11/2018 | |

OTHER PUBLICATIONS

Dong et al., "An Image Correlation Procedure for Digitally Reconstructed Radiographs and Electronic Portal Images", Int. J. Radiation Oncology Biol. Phys., vol. 33, No. 5, 1995, pp. 1053-1060.

Hissoiny et al., "GPUMCD: a new GPU-Oriented Monte Carlo dose calculation platform", physics.med-ph, Jan. 2011, 28 pp.

Jung et al., "Flexible Gd2O2S: Tb scintillators pixelated with polyethylene microstructures for digital x-ray image sensors", J. Micromech. Microeng. 19, 2009, 10pp.

Lo et al., "Hardware acceleration of a Monte Carlo simulation for photodynamic treatment planning", Journal of Biomedical Optics, vol. 14(1), Jan./Feb. 2009, pp. 014019-1 thru 014019-11.

Mackie et al., "Tomotherapy: a new concept for the delivery of dynamic conformal radiotherapy.", Medical Physics 20, 1709 (1993); doi: 10.1118/1.596958, Jun. 4, 1998, 1709-1719.

Osher et al., "Fast Linearized Bregman Iteration for Compressive Sensing and Sparse Denoising", 2008, pp. 1-19.

Ruchala et al., "Megavoltage CT image reconstruction during tomotherapy treatments", Phys. Med. Biol. vol. 45, 2000, pp. 3545-3562.

Schonberg, "The History of the Portable Linear Accelerator", American Association for Physicists in Medicine, downloaded from the internet: https://www.aapm.org/meetings/2001AM/pdf/7221-68900.pdf, 2001, pp. 1-14.

Weidlich et al., "Characterization of a Novel Revolving Radiation Collimator", Cureus, vol. 10, No. 2, Feb. 2, 2018, pp. 1-9.

Zaman et al., "Scintillating Balloon-Enabled Fiber-Optic System for Radionuclide Imaging of Atherosclerotic Plaques", J Nucl Med 56(5), 2015, 771-777.

\* cited by examiner

REVOLVING RADIATION COLLIMATOR

CROSS-REFERENCES TO RELATED APPLICATIONS

The present application is a Continuation of U.S. application Ser. No. 15/971,861 filed May 4, 2018 (now U.S. Pat. No. 11,058,892); which claims the benefit of U.S. Provisional Appln No. 62/502,472 filed May 5, 2017 and PCT Appln No. PCT/US2017/038256 filed Jun. 20, 2017, the disclosures which are incorporated herein by reference in their entirety for all purposes.

The present application is related to PCT Application Serial No. PCT/US2017/054880 filed Oct. 3, 2017, which is assigned to the same assignee as the present application and incorporated by herein by reference in its entirety for all purposes.

BACKGROUND

The overarching goal of the collimator system is to deliver a beam of radiation produced by a source (for example a LINAC) to a target (for example a tumor in a patient's brain). Because it is desirable to irradiate a tumor, but generally not desirable to irradiate surrounding healthy tissue, the size and the shape of each beam is of critical importance. In order to control the shape (for example diameter or 2D cross sectional area) of a beam of radiation, a collimator is used. A collimator is generally a piece of dense radiopaque metal that substantially blocks a beam of radiation except where a formed or machined hole allows the radiation to be transmitted through. A larger radiation footprint may be produced by the radiation source (for example a LINAC or cobalt), but only those particles aligned to pass through the collimator will be permitted through to reach the target, the excess being absorbed or scattered internally. In addition to the tubular channels of machined or formed collimators, another pre-existing type is a "multi leaf collimator" using multiple thin tungsten plates moving in and out of the beam path to generate the desired beam exposure shape during treatment. This complex mechanism is complex, bulky, expensive, and prone to mechanical failure.

Different size and shape radiation treatment targets require different size and shape beams of radiation. There exists a need for systems and methods that allow for radiation beams to be changed in a rapid and predictable manner. There is a need for collimating radiation beams without excess leakage of radiation around the collimator. There is further a need for such systems to remain small, reliable and low cost.

BRIEF SUMMARY

The invention relates to the field of radiation therapy, and in particular, to collimator systems and associated methods of controlling the size and shape of radiation treatment beams during radiation therapy.

In a first aspect, the invention pertains to a radiation collimator assembly that includes a rotatable collimator body or collimator wheel having multiple collimator channels defined therein. In some embodiments, the collimator channels extend longitudinally perpendicular to the rotational axis of the collimator wheel, extending from the perimeter of the wheel, passing through the center and out to the opposite perimeter of the wheel. The collimator wheel is at least partly surrounded by a collimator shield, excepting at least the portion having the selected collimator channel that is aligned with the radiation source and the patient target to allow passage of the radiation beam therethrough. In some embodiments, the posterior, LINAC-facing portion of the collimator wheel is ensheathed in shielding to prevent stray radiation from passing through non-selected collimator channels. The collimator shield is fabricated from a suitable radiation absorptive material, typically tungsten or tungsten alloy, so as to block and absorb any scattered radiation emitted from orifices of non-aligned channels.

In another aspect, the collimator body is motorized and precisely indexed for rapid and exacting computer-controlled positioning of the selected collimator channel geometry with the radiation source, thereby delivering a desired beam shape to the precise dimensions required at the target. By using a revolving collimator wheel, multiple sizes of the beam may be utilized during one treatment, quickly and automatically switching between two or more selected collimators.

These collimation assemblies have the advantage of being rapidly changeable by computer control, while remaining small, reliable in their simplicity and low in cost. Moreover, such assemblies can utilize a single motor to switch between select one or more collimator channels. The aspects of the invention described herein allow for a more reliable radiation collimator that can quickly and precisely change X-ray exposure from 1 mm to 30 mm diameter at isocenter, and can function more reliably than many prior art collimators. Such collimator assemblies enable rapid, automated (motorized and computer controlled) changing of beam aperture in the service of therapeutic radiation delivery, for example to treat brain tumors.

The collimator systems described herein allow for beam collimation without requiring use of a conventional block collimator and/or multi-leaf collimator system, such as those commonly used in conventional radiation treatment systems, which are bulky and prone to mechanical malfunction over time.

In one aspect, an exemplary radiation collimator assembly includes a radiation source and a collimator wheel rotatable about a rotational axis thereof. The collimator wheel has multiple collimator channels that include a first and second collimator channel defined within the collimator wheel that are arranged substantially perpendicular to the rotational axis of the collimator wheel. The collimator can include additional channels, for example three or more channels. The collimator can include any number of channels desired (e.g. 2, 3, 4, 5, 6, 7, 8, 9, 10 channels or more). In some embodiments, each of the first and second collimator channels pass through a center of the collimator wheel through which the rotational axis extends. Preferably, at least some of the collimator channels are of differing sizes and/or shapes. In some embodiments, the multiple collimator channels are distributed at regular intervals along the collimator wheel.

In another aspect, the first and second collimator channels are selectable by rotationally moving the collimator wheel to align one of the first and second collimator channels with the radiation source. Selective rotation of the collimator wheel can be facilitated by a motor and control unit operably coupled to the wheel. In some embodiments, the collimator assembly includes a motor operably coupled with the collimator wheel so as to rotate the collimator wheel about the rotational axis; and a control unit operably coupled with the motor to control rotation of the collimator wheel to a collimator position corresponding to alignment of a selected collimator channel with the radiation source. In some embodiments, the control unit is communicatively coupled with one or more sensors configured to detect the collimator position. The one or more sensors can include one or more encoder readers and the collimator wheel includes multiple markers positioned thereon so that detection of a marker corresponds to alignment of a corresponding collimator channel.

In another aspect, radiation treatment systems utilizing such collimator assemblies are provided herein. An exemplary treatment system can include a radiation collimator assembly, such as described above, that is configured to deliver a radiation beam from a radiation source through one or more selected collimator channels of the collimator wheel to a target within a patient. Such a system can include a motor operably coupled with the collimator wheel so as to rotate the collimator wheel about the rotational axis and a control unit operably coupled with the motor to control rotation of the collimator wheel to positions corresponding to alignment of one or more selected collimator channel with the radiation source. The control unit is configured rotate the collimator wheel to align one or more selected collimator channels with the radiation source, the one or more selected collimator channels corresponding to one or more desired therapy beams.

In another aspect, the treatment system includes a collimator shield. The collimator shield can be configured to surround at least a portion of the collimator body during delivery of therapy so as to block radiation from non-aligned collimator channels while allowing passage of a therapy beam from the selected, aligned collimator channel. In some embodiments, the collimator shield substantially surrounds a portion of the collimator wheel facing the radiation source except for the entry orifice of the selected, aligned collimator channel. In some embodiments, the collimator shield substantially surrounds the collimator body except for an aperture at an apex of the shield through which includes the exit orifice of the selected aligned collimator channel is exposed as well as a passage at the inlet orifice of the aligned channel to allow entry of the radiation beam through the selected channel. While a conically shaped shield is depicted in the embodiments presented herein, it is appreciated that the collimator shield could be formed in various different shapes so long as the shield allows radiation to pass through the selected, aligned channel while blocking radiation emitted from non-selected channels and from around the shield itself, resulting in minimal radiation leakage around the intended beam.

In yet another aspect, the treatment system can include an alignment verification mechanism. Such a verification feature can include an optical alignment feature, such as an optical laser light mechanism that directs a laser light beam through the selected collimator channel and detects the laser light beam emanating from an exit orifice. In some embodiments, the treatment system further includes one or more imaging devices for monitoring a patient during treatment.

In some embodiments, the collimator includes a collimator body having a pivot feature about which the collimator body is rotatable about a pivotal axis and multiple collimator channels extending through the collimator body, each being substantially perpendicular to the pivotal axis about which the collimator body is revolved. In some embodiments, each of the multiple collimator channels intersects the pivotal axis.

In another aspect, methods of delivering therapy beams of differing size and/or shape to a target in a patient during therapy are provided herein. An exemplary method includes selecting a first collimator channel from multiple collimator channels in a collimator body, the selected first collimator channel corresponding to a desired first therapy beam. The collimator body is rotatable within the treatment system along a rotational axis of the collimator body and the multiple collimator channels differ in size and/or shape and extend substantially perpendicular to the rotational axis. Next, the collimator body is rotated along the rotational axis until the selected first collimator channel is aligned with the radiation source, then a first particle beam is transmitted from a radiation source through the selected first collimator channel so as to direct the desired first therapy beam to the target within the patient. Such methods can further include selecting a second collimator channel in the collimator body, the selected second collimator channel corresponding to a desired second therapy beam differing from the first therapy beam in size and/or shape. The collimator body is then rotated along the rotational axis until the selected second collimator channel is aligned with the radiation source and then a second particle beam is transmitted from the radiation source through the selected second collimator channel so as to direct the desired second therapy beam to the target within the patient. In some embodiments, rotating the collimator body until the selected first collimator channel is aligned comprises rotating the collimator body until a sensor of a control unit of the system detects a marker disposed on the collimator body indicating a collimator position that corresponds to alignment of the first collimator channel. Such methods can further include validating alignment of the first collimator channel with the radiation source by transmitting a laser light beam through the collimator channel and detecting the laser light beam emitted from an exit aperture of the first collimator channel.

Various aspects and details of the invention can be further understood by referring to the exemplary embodiments depicted in the figures and the description provided below.

DETAILED DESCRIPTION

The invention relates generally to radiation treatment systems and methods of use, in particular collimator systems provide selective control and delivery of collimated beams of radiation.

Figure 1:
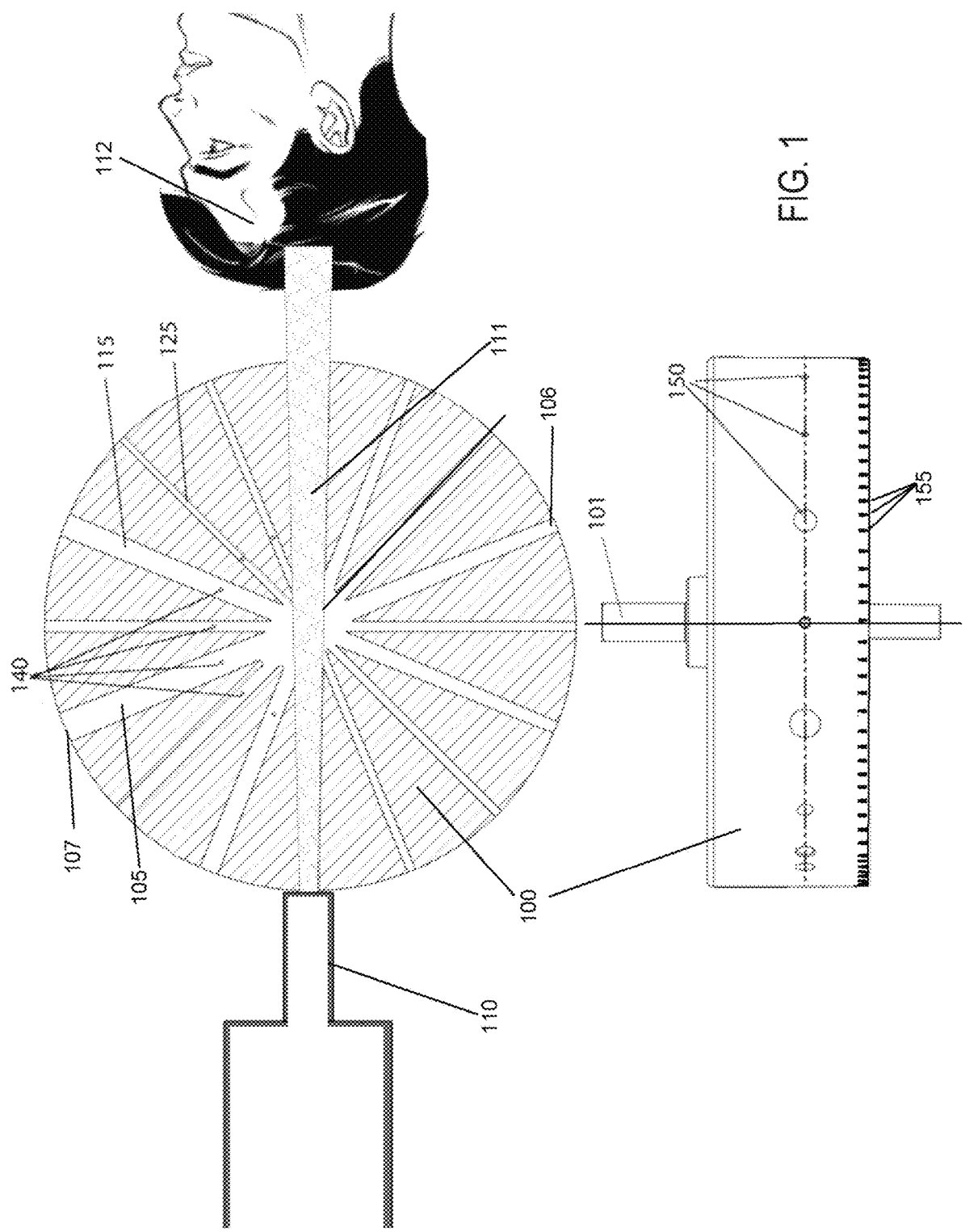
FIG. 1 shows a cross section of an example revolving collimator wheel having collimator channels passing therethrough.

FIG. 1 shows a cross sectional view of a revolving collimator wheel 100 having collimator channels 140 passing therethrough. Collimator wheel 100 has longitudinally extending channels or collimator channels 105, 115 and 125 defined therein, for example machined through the body of collimator wheel 100. The figure shows multiple other channels that are not labeled for the sake of clarity of the drawing. The collimator channels may be of various sizes, diameters or shapes. In some embodiments, each collimator channel is of a different diameter. For example, as shown in FIG. 1, collimator channel 105 is of larger bore than collimator channel 115, which is of larger bore than collimator channel 125. Each collimator channel extends from a radiation entrance aperture 106 to an exit aperture 107. In some embodiments, the size of the entrance aperture 106 is smaller than that of the exit aperture 107 to facilitate a sharp falloff of radiation dose at the margins of the irradiated area. The collimator wheel 100 is rotated so that a selected collimator channel is aligned with a radiation source 110 to allow passage of a particle radiation beam 111 through the selected channel, thereby providing a desired therapy beam to a target 112 in the patient. In a side profile of collimator wheel 100 shown at the bottom of FIG. 1, the entrance and exit apertures 150 are visible about the circumference collimator wheel 100 turns on axis 101. In this example, collimator wheel 100, couples with a 50:1 reduction gearbox and electric motor. In some embodiments, channel 105 and exit aperture 107 are round. It is appreciated that in alternative embodiments, the channels may be of any size or shape, for example square. Collimator wheel 100 can be formed of any suitable material, for example machined from a titanium alloy. While collimator wheel 100 is shown as being oriented vertically relative to the surface on which the patient rests, it is appreciated that the collimator wheel 100 could be configured in any orientation so long as the treatment beams passing through the collimator channels are directed to the target. Further, while the collimator wheel is shown as having eight collimator channels it is appreciated that such collimator wheels could include more or fewer collimator channels.

Figure 2:
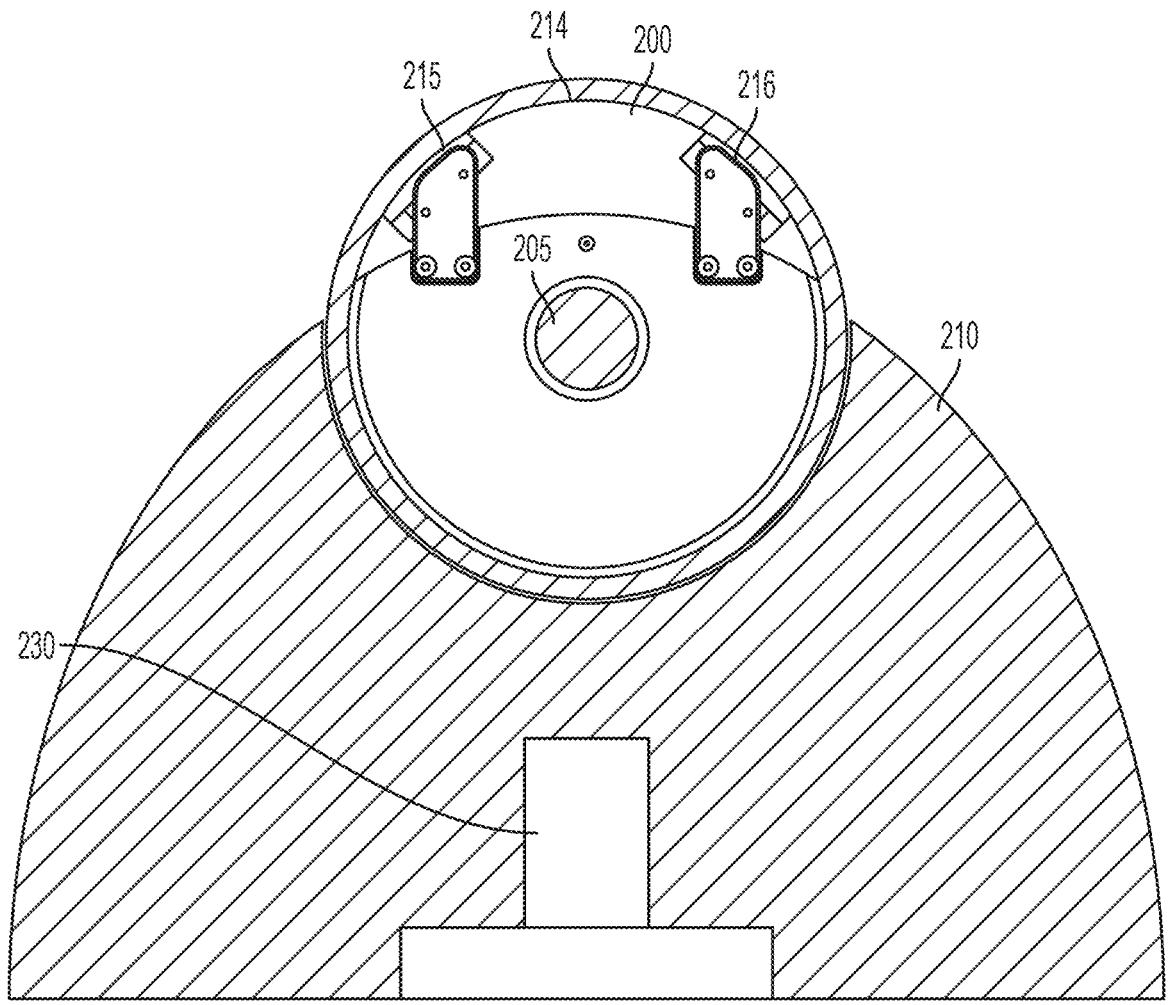
FIG. 2 shows an example revolving collimator wheel mounted upon a conical shield, the collimator wheel having magnetic encoder trackers that sense when the wheel has been brought into a desired collimator position.

FIG. 2 shows a cross section of a revolving collimator wheel 200 mounted upon a collimator shield 210, and rotating between collimator positions on axis 205. In this embodiment, the collimator shield 210 substantially ensheaths the portion of the collimator wheel facing the radiation source so as to prevent radiation from entering non-aligned collimator channels, and of a thickness designed to otherwise provide shielding against leakage for the radiation source. The rotational position of the collimator wheel can be precisely controlled by a control system by use of one or more sensors or encoders that monitor the position of the collimator wheel 200, for example by detecting markers disposed on the periphery of the collimator wheel. In this embodiment, the position of the collimator wheel is precisely monitored by encoder reader heads 215 and 216, which track a thin tape-like encoder strip affixed to the inner rim 214 of collimator wheel 100, adjacent to the path of reader heads 215 and 216. The control system detects signals produced by precisely placed changes in the electromagnetic interaction between the encoders and the encoder strip. Using this combination of encoder strip affixed to internal rim 214 and encoder reader heads, the control system senses when the wheel has been brought into the desired collimator position. Also shown in the cross section of collimator shield 210 is a LINAC head 230, which is the source of the radiation delivered to the entrance aperture of a selected collimator. In some embodiments, an ion chamber for measuring radiation intensity is included in the collimator shield between the LINAC head 230 and collimator wheel 200. Alternative positional encoder schemes could include mechanical stops such as gear teeth and divots, and/or optically sensed position markers.

In one aspect, the collimator assembly and control system described above are incorporated into a treatment system. The control system includes a processor configured to facilitate controlled rotation of the collimator wheel to select positions corresponding to alignment of a selected collimator channel with the radiation source, the selected collimator channel corresponding to a desired treatment beam. In some embodiments, the treatment system includes a user interface that allows a treating physician to select one or more treatment beams associated with one or more collimator channels. In other embodiments, the control system automatically determine one or more collimator channels corresponding to a selected course of treatment.

Figure 3:
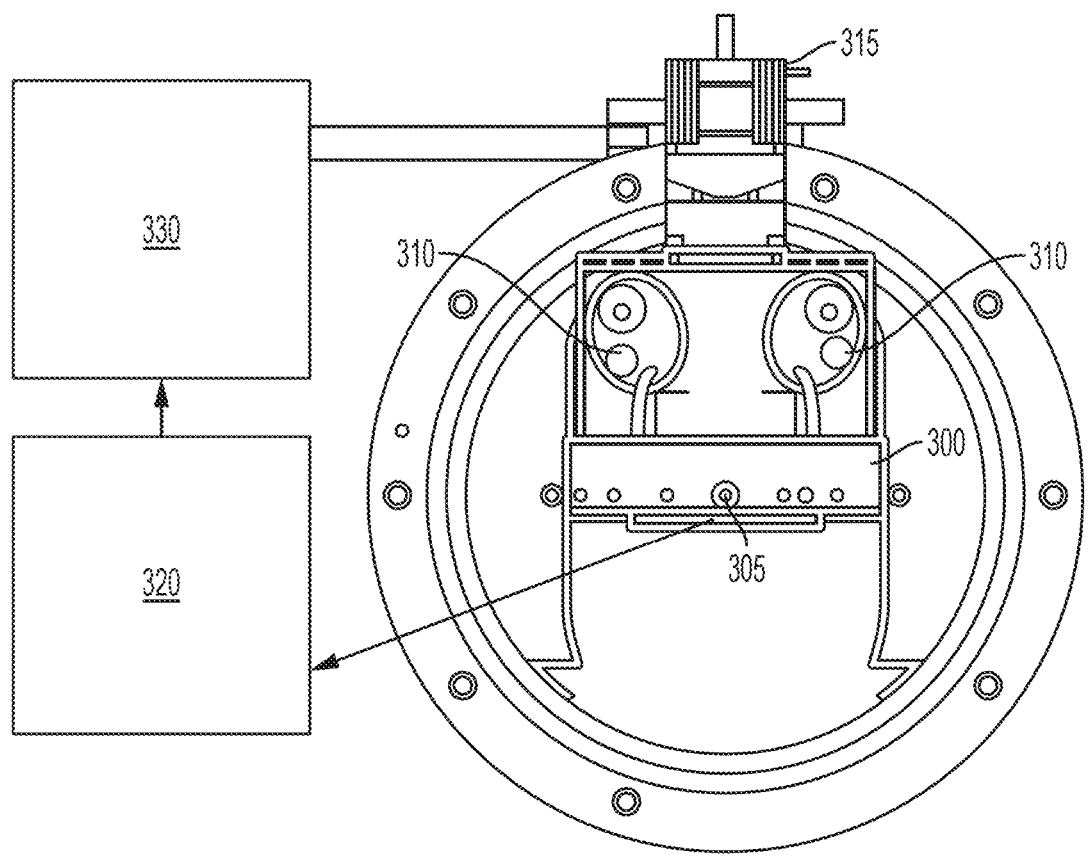
FIG. 3 shows the apex of an example conical shield, including the exit openings of the collimator channels of the collimator wheel and cameras for monitoring the patient.

FIG. 3 shows the apex of the conical shield, including the exit openings of the collimator channels and cameras for monitoring the patient. Collimator wheel 300 is visible edge-on, including selected channel exit aperture 305 and other apertures that are not identified and thus not aligned with the LINAC (underlying and not visible). Motor 315 turns collimator wheel 305 to a selected position in which the desired aperture is aligned with the LINAC. In some embodiments, the system includes one or more cameras to, for example cameras 310, positioned to permit the patient to be monitored while undergoing radiation treatment. Encoder interpretation computer subsystem 320 receives signals from encoder reader heads (see FIG. 2) to compute the precise rotational position of collimator wheel 300, and hence the position of any of the selectable collimator channels. For example, in a feedback loop, motor control computer subsystem 330 serves to activate motor 315 until encoders indicate that the selected collimator is aligned with the LINAC. In one aspect, the system is configured to change the collimator wheel position between multiple positions associated with select collimator channels during therapy so as to differing sizes of treatment beams to the target.

Figure 4:
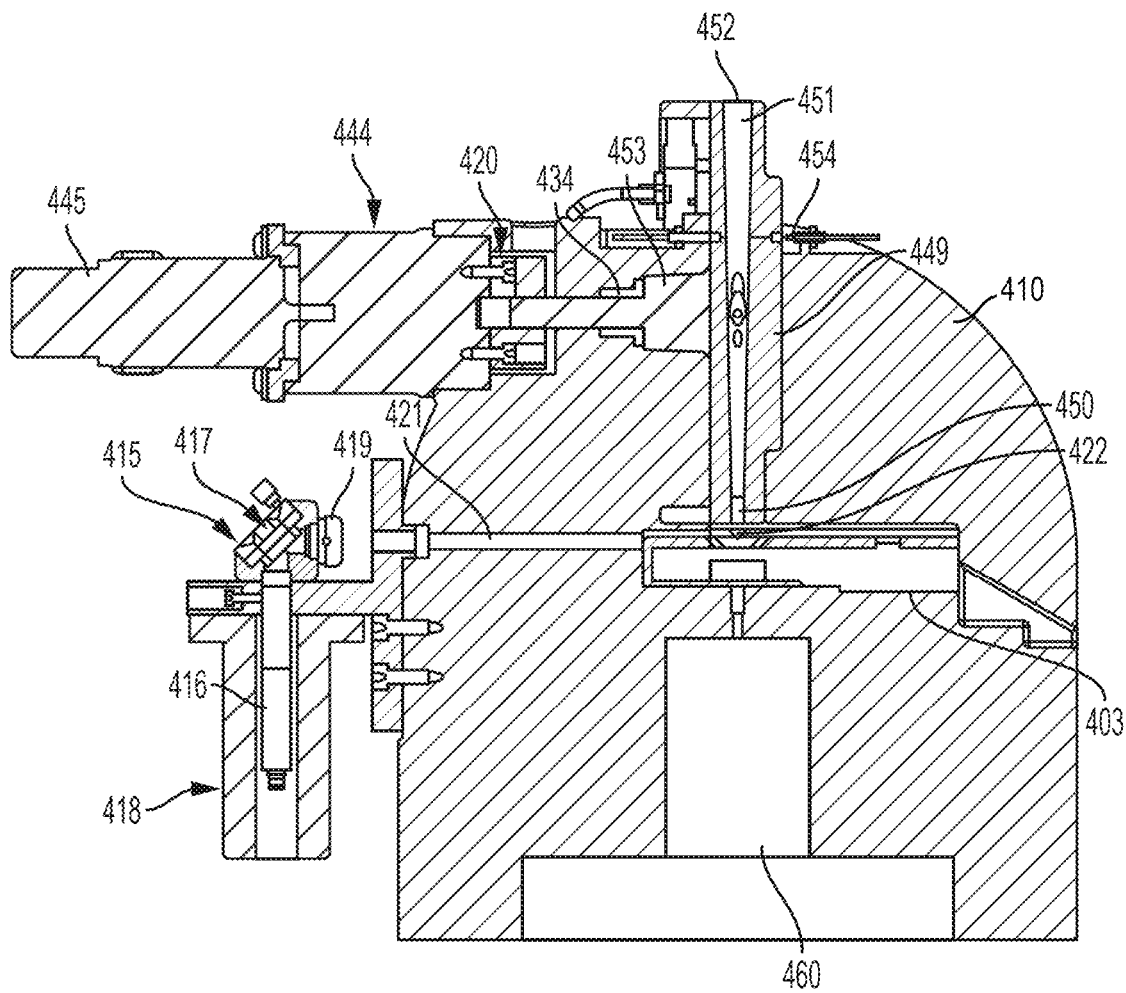
FIG. 4 shows an example collimator wheel and associated motor configured to drive between positions, and a linear accelerator that passes radiation through the collimator wheel and associated features.

FIG. 4 shows a cross-sectional view of the collimator wheel in the context of the motor that drives between positions and a linear accelerator that passes radiation through an aligned collimator channel and associated features.

As shown, collimator wheel 449 has selected and aligned channel 451 with exit aperture 452 and entrance aperture 450. Collimator shield 410 surrounds the collimator wheel 449 along the portion facing the radiation source to allow passage of the particle beam through the inlet and exit orifices of channel 451 while preventing radiation from entering non-aligned channels. In this embodiment, collimator wheel 449 is selectively turned into the desired position via shaft 453 with bushing 434, shaft 453 being connected with gearbox 444 via coupling bracket and base 420. Gearbox 44 is coupled to and driven by motor 445, and provides a reduction in revolutions at a pre-defined ratio, permitting very fine control of the degree to which the collimator wheel is turned and aligned with the radiation source, the LINAC head 460 and distal margin of LINAC body 461. The pre-defined ratio can be 10:1, 20:1, 30:1, 40:1, 50:1, 60:1, 70:1, 80:1, 90:1 or any ratio suitable for a given geometry of the collimator wheel and treatment system and desired resolution of adjustment. In this embodiment, energy exiting LINAC head 460 enters sealed ion chamber 403 which permits monitoring of dose, dose rate and field symmetry by virtue of the fact that radiation that enters the ion chamber will produce a measureable ionization current that is proportional to the x-ray beam intensity.

In this embodiment, mechanical alignment is optimized using optical beam techniques. This has the advantage of maximizing the transfer of radiation from the ion chamber 403 into entrance aperture 450. For this purpose, the system includes laser shield mount holding laser 416, the beam from which is bent at a right angle by mirror 415 and directed into diaphragm iris lens 419 after which the laser light passes through shield bore 421 defined in shield 410 to reach the beam path right angle optical mirror 422. Because the beam path right angle optical mirror 422 is reflective to light but transparent to radiation, a properly aligned collimator can be detected by a laser beam being emitted from exit aperture 452 of collimator 451, while maintaining functionality of the primary radiation delivery alignment, a function useful in initial validation and verification of each machine.

Figure 5:
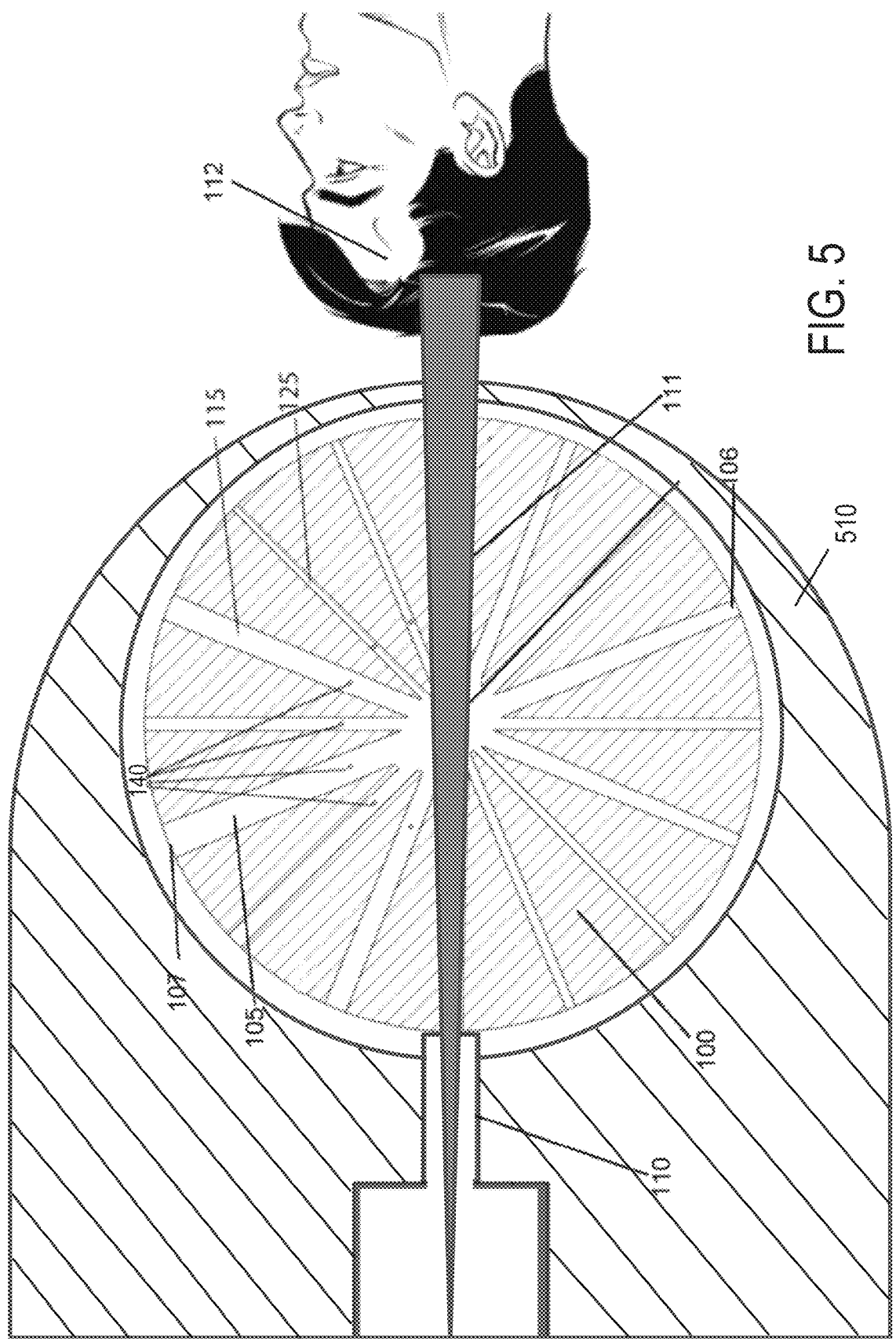
FIG. 5 shows another example conical shield surrounding a periphery of the collimator wheel to cover orifices of non-aligned channels.

FIG. 5 shows another example system with the same or similar collimator wheel and associated components shown in FIG. 1 and a conical collimator shield 510 that substantially surrounds the periphery of the collimator wheel so as to block and absorb radiation emitted from orifices of non-aligned collimator channels while allowing passage of a particle beam 111 from the radiation source 110 through the selected, aligned collimator channel to provide a desired therapy beam to the target 112. In this embodiment, the collimator shield 510 covers any orifices of non-aligned channels, and its resulting greater thickness minimizes radiation leakage from linear accelerator 110. In some embodiments, the shield can cover less than all orifices of non-aligned channels. It is appreciated that in any of the embodiments herein, the shield can include multiple shield components to cover orifices of non-aligned channels and is not required to be a unitary component. Various configurations of the shield can be realized in accordance with the concepts described herein.

While these components are shown in a particular arrangement in this example, it is appreciated that alternative configurations could be realized utilizing various other means of rotating the collimator wheel as would be understood by one of skill in the art. In addition, it is appreciate that certain elements could be omitted, such as the cameras, ion chamber and optical beam alignment features, while still retaining certain advantageous aspects of the invention described above.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A radiation collimator assembly comprising:
   a radiation source; and
   a collimator body rotatable about a rotational axis thereof, wherein the collimator body has a plurality of collimator channels, the plurality of collimator channels including at least:
      a first collimator channel defined within the collimator body, and
      a second collimator channel defined within the collimator body,
      wherein the first and second collimator channels are arranged substantially perpendicular to the rotational axis of the collimator body;
   wherein the collimator assembly is configured to collimate a radiation beam transmitted from the radiation source through one or more selected collimator channels of the collimator body to a target within a patient; and
   wherein the collimator body is configured to be disposed between the radiation source and the target, such that the radiation beam enters the collimator body at a first point along a periphery of the collimator body and exits the collimator body at a second point along the periphery of the collimator body.

2. The radiation collimator assembly of claim 1 wherein each of the first and second collimator channels passes through a center of the collimator body through which the rotational axis extends.

3. The radiation collimator assembly of claim 1 wherein the collimator body has a circular disc shape having a diameter greater than a thickness thereof.

4. The radiation collimator assembly of claim 1, wherein each of the first and second collimator channels has a proximal opening adjacent the radiation source that is smaller than a distal opening configured to be nearer the target.

5. The radiation collimator assembly of claim 1, wherein each of the first and second collimator channels is circular.

6. The radiation collimator assembly of claim 1, wherein the collimator body and plurality of collimator channels are configured and arranged relative to the radiation source to create a radiation beam of up to 30 mm in diameter at the target.

7. The radiation collimator assembly of claim 1, wherein each of the first and second channels has a diameter that increases along a length thereof in a direction configured to be toward the target.

8. The radiation collimator assembly of claim 1, wherein the first and second collimator channels are of differing sizes and/or shapes.

9. The radiation collimator assembly of claim 1, wherein the plurality of collimator channels are distributed at regular intervals along the collimator body.

10. The radiation collimator assembly of claim 1, wherein the plurality of collimator channels comprises three or more collimator channels.

11. The radiation collimator assembly of claim 1, wherein the first and second collimator channels are selectable by rotationally moving the collimator body to align one of the first and second collimator channels with the radiation source, wherein only a single channel is aligned with the radiation source at a time.

12. The radiation collimator assembly of claim 11, further comprising:
   a motor operably coupled with the collimator body so as to rotate the collimator body about the rotational axis thereof; and
   a control unit operably coupled with the motor to control rotation of the collimator body to a collimator position corresponding to alignment of a selected collimator channel with the radiation source.

13. The radiation collimator assembly of claim 12, wherein the control unit is communicatively coupled with one or more sensors configured to detect the collimator position.

14. The radiation collimator assembly of claim 1, further comprising:

a collimator shield substantially surrounding at least a portion of the collimator body that covers non-aligned collimator channels to inhibit passage of radiation therethrough while allowing passage of a radiation beam through the one or more selected collimator channels.

15. The radiation collimator assembly of claim 1, further comprising:
an optical beam alignment feature configured to monitor or validate alignment of the one or more selected collimator channels with the radiation source.

16. A radiation treatment system comprising:
the radiation collimator assembly of claim 1, wherein the collimator assembly is configured to deliver the radiation beam from the radiation source through the one or more selected collimator channels of the collimator body to the target within the patient;
a motor operably coupled with the collimator body so as to rotate the collimator body about the rotational axis; and
a control unit operably coupled with the motor to control rotation of the collimator body to positions corresponding to alignment of the one or more selected collimator channels with the radiation source.

17. The radiation treatment system of claim 16, wherein the control unit is configured to rotate the collimator body to align the one or more selected collimator channels of the plurality of collimator channels with the radiation source, the one or more selected collimator channels corresponding to one or more desired therapy beams.

18. The radiation treatment system of claim 16, wherein any of:
each of the plurality of collimator channels passes through a center of the collimator body through which the rotational axis extends;
wherein the collimator body has a circular disc shape having a diameter greater than a thickness of the collimator body;
each of the first and second collimator channels has a proximal opening adjacent the radiation source that is smaller than a distal opening configured to be nearer the target;
wherein each of the first and second collimator channels is circular;
wherein the collimator body is configured for collimation of radiation beams for therapy; and
wherein the collimator body and plurality of collimator channels are configured and arranged relative to the radiation source to create a radiation beam of up to 30 mm in diameter at the target.

19. A radiation collimator assembly comprising:
a radiation source; and
a collimator body rotatable about a rotational axis thereof, wherein the collimator body has a plurality of collimator channels, the plurality of collimator channels including at least:
a first collimator channel defined within the collimator body, and
a second collimator channel defined within the collimator body,
wherein the first and second collimator channels are arranged substantially perpendicular to the rotational axis of the collimator body;
wherein the collimator assembly is configured to collimate a radiation beam transmitted from the radiation source through one or more selected collimator channels of the collimator body to a target within a patient; and
wherein the collimator body is configured to be disposed between the radiation source and the target,
wherein the first and second collimator channels are selectable by rotationally moving the collimator body to align one of the first and second collimator channels with the radiation source, wherein only a single channel is aligned with the radiation source at a time,
a motor operably coupled with the collimator body so as to rotate the collimator body about the rotational axis thereof; and
a control unit operably coupled with the motor to control rotation of the collimator body to a collimator position corresponding to alignment of a selected collimator channel with the radiation source,
wherein the control unit is communicatively coupled with one or more sensors configured to detect the collimator position,
wherein the one or more sensors comprise one or more encoder readers and the collimator body includes a plurality of markers positioned so as to correspond to alignments of the plurality of collimator channels.

20. A collimator for collimating a radiation beam generated by a radiation source for transmission to a target within a patient, the collimator comprising:
a collimator body having a plurality of collimator channels extending through the collimator body;
a pivot feature about which the collimator body is rotatable about a rotational axis of the collimator body so as to align a selected collimator channel of the plurality of collimator channels with the radiation source to facilitate collimation of a radiation beam transmitted from the radiation source to the target, wherein the radiation beam enters the collimator body at a first point along a periphery of the collimator body and exits the collimator body at a second point along the periphery of the collimator body; and
wherein each of the plurality of collimator channels is perpendicular to the rotational axis about which the collimator body is rotated.

21. The collimator of claim 20, wherein each of the plurality of collimator channels intersects the rotational axis.

22. The collimator of claim 20, wherein the collimator body has a circular disc shape having a diameter greater than a thickness of the collimator body.

23. The collimator of claim 20, wherein each of the plurality of collimator channels has a proximal opening adjacent the radiation source that is smaller than a distal opening configured to be nearer the target.

24. The collimator of claim 20, wherein each of the plurality of collimator channels is circular.

25. The collimator of claim 20, further comprising:
a plurality of markers disposed at regular intervals along the periphery of the collimator body to facilitate alignment of the selected collimator channel with the radiation source by a control system.

26. A method of collimating a radiation beam, the method comprising:
selecting a first collimator channel from a plurality of collimator channels in a collimator body, the selected first collimator channel corresponding to a first therapy beam of a desired first size or shape, wherein the collimator body is rotatable along a rotational axis of the collimator body, wherein the plurality of collimator channels are of differing sizes and/or shapes and extend perpendicular to the rotational axis;

rotating the collimator body along the rotational axis thereof until the selected first collimator channel is aligned with a radiation source; and transmitting a radiation beam from the radiation source through the selected first collimator channel, thereby collimating the radiation beam to the desired first size or shape at a target within a patient, wherein the radiation beam enters the collimator body at a first point along a periphery of the collimator body and exits the collimator body at a second point along the periphery of the collimator body.

27. The method of claim 26, further comprising:

selecting a second collimator channel from the plurality of collimator channels in the collimator body, the selected second collimator channel corresponding to a second desired size or shape that differs from the first therapy beam;

rotating the collimator body along the rotational axis until the selected second collimator channel is aligned with the radiation source; and transmitting a second radiation beam from the radiation source through the selected second collimator channel, thereby collimating the radiation beam to the desired second size or shape at the target.

28. The method of claim 27, wherein any of:

each of the plurality of collimator channels passes through a center of the collimator body through which the rotational axis extends;

wherein the collimator body has a circular disc shape having a diameter greater than a thickness of the collimator body;

each of the first and second collimator channels has a proximal opening adjacent the radiation source that is smaller than a distal opening nearer the target;

wherein each of the first and second collimator channels is circular;

wherein the collimator body is configured for collimation of radiation beams for therapy; and wherein the collimator body and plurality of collimator channels are configured and arranged relative to the radiation source to create a radiation beam of up to 30 mm in diameter at the target.

29. The method of claim 26, further comprising:

validating alignment of the first collimator channel with the radiation source by transmitting a laser light beam through the first collimator channel and detecting the laser light beam emitted from an exit aperture of the first collimator channel.

30. A method of collimating a radiation beam, the method comprising:

selecting a first collimator channel from a plurality of collimator channels in a collimator body, the selected first collimator channel corresponding to a first therapy beam of a desired first size or shape, wherein the collimator body is rotatable along a rotational axis of the collimator body, wherein the plurality of collimator channels are of differing sizes and/or shapes and extend perpendicular to the rotational axis;

rotating the collimator body along the rotational axis thereof until the selected first collimator channel is aligned with a radiation source; and transmitting a radiation beam from the radiation source through the selected first collimator channel, thereby collimating the radiation beam to the desired first size or shape at a target within a patient, wherein rotating the collimator body until the selected first collimator channel is aligned comprises rotating the collimator body until a sensor of a control unit detects a marker disposed on the collimator body indicating a collimator position that corresponds to alignment of the first collimator channel.

\* \* \* \* \*